United States Patent [19]
Trainer

[11] Patent Number: 6,104,490
[45] Date of Patent: Aug. 15, 2000

[54] MULTIPLE PATHLENGTH SENSOR FOR DETERMINING SMALL PARTICLE SIZE DISTRIBUTION IN HIGH PARTICLE CONCENTRATIONS

[75] Inventor: Michael N. Trainer, Telford, Pa.

[73] Assignee: Microtrac, Inc., Montgomeryville, Pa.

[21] Appl. No.: 09/211,373

[22] Filed: Dec. 14, 1998

[51] Int. Cl.7 .................................................... G01N 15/02
[52] U.S. Cl. ........................................... 356/336; 356/342
[58] Field of Search .................................... 356/336, 335, 356/337, 342, 343

[56] References Cited

U.S. PATENT DOCUMENTS

| 4,497,577 | 2/1985 | Sato et al. | 356/342 |
| 5,094,532 | 3/1992 | Trainer et al. | 356/336 |
| 5,416,580 | 5/1995 | Trainer | 356/336 |
| 5,576,827 | 11/1996 | Strickland et al. | 356/336 |

Primary Examiner—Frank G. Font
Assistant Examiner—Layla G. Lauchman
Attorney, Agent, or Firm—Wood, Herron & Evans, LLP

[57] ABSTRACT

A multiple pathlength sensor is disclosed that is installed substantially within a process stream containing particles at high concentrations. The sensor includes a transparent surface for receiving the first and the second light energy emissions projected by first and second light delivery arrangements. The first and second light energy emissions penetrate the transparent surface and enter the sensor in a first directional path. A first light deflecting surface modifies the first and second light energy emissions to travel into a second directional path through the sensor. A first passage exposed to the process stream is sized to receive particles of a first predetermined size range. The first light energy emission in the second directional path is projected through the first passage to irradiate the particle ensemble therein. A second passage exposed to the process stream is sized to receive particles of a second predetermined size range. The second light energy emission in the second directional path is projected through the second passage to irradiate the particle ensemble therein. A second light deflecting surface receives the light energy projected through the first and second passages and the light energy scattered by the particle ensemble in each of the first and said second passages. The second deflecting surface directionally modifies the light energy it receives to follow a third directional path through the sensor to the transparent surface, where the light energy escapes the sensor and is collected by a light collection arrangement.

7 Claims, 5 Drawing Sheets

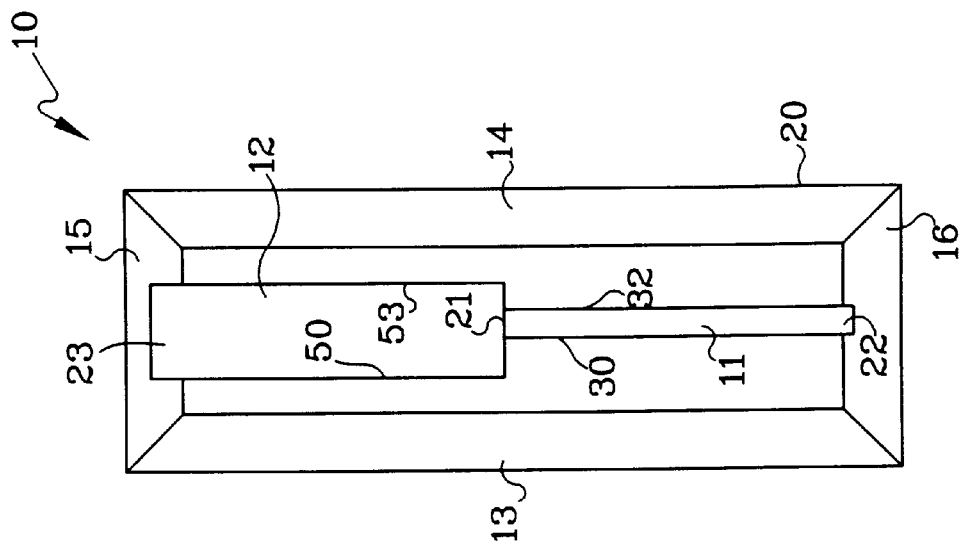
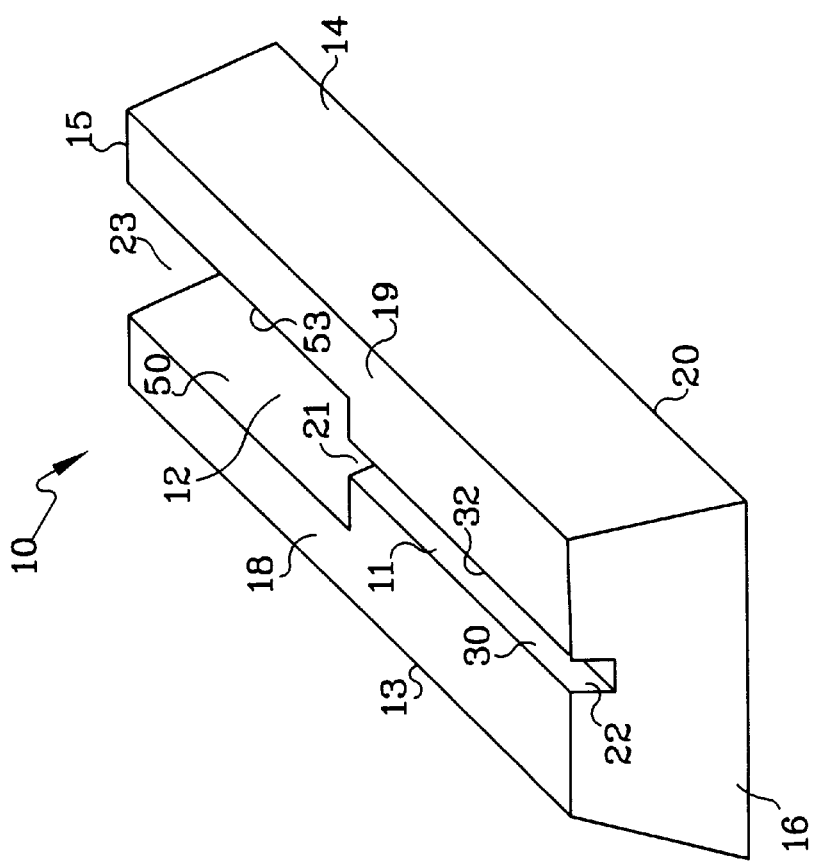
Fig. 3B
Fig. 3A

MULTIPLE PATHLENGTH SENSOR FOR DETERMINING SMALL PARTICLE SIZE DISTRIBUTION IN HIGH PARTICLE CONCENTRATIONS

CROSS-REFERENCE TO RELATED APPLICATIONS

This present application is related to applicant's co-pending patent application, Ser. No. 09/211,374, entitled "A SYSTEM FOR DETERMINING SMALL PARTICLE SIZE DISTRIBUTION IN HIGH PARTICLE CONCENTRATIONS", filed on an even date herewith and assigned to a common assignee with the present invention.

BACKGROUND OF THE INVENTION

1. Field of the Invention

The present invention relates generally to the field of determining particle size distribution and more specifically to a multiple pathlength sensor used for measuring particle size distribution in process streams having high particle concentrations.

2. Discussion of the Related Art

The measurement of particle size distribution finds use in the process industries in the manufacture of pharmaceuticals, chemicals, abrasives, ceramics, pigments and the like, where the particle size affects the quality of the manufactured product.

A number of methods presently exist for determining the size distribution of particulate material for particles in the approximate size range of 0.1 to 1000 microns in diameter. The conventional method of measurement at high concentrations is dynamic light scattering, as taught by U.S. Pat. No. 5,094,532 to Trainer et al, patented Mar. 10, 1992. This patent discloses a fiber optic Doppler anemometer and method that directs a beam of light into a scattering medium that contains particles in Brownian motion. The frequency of the scattered light is compared to non-scattered light emitted from the scattering medium and results in the generation of a first signal having a magnitude that is indicative of the difference in frequency between the scattered light and the non-scattered light. A second signal is generated having a magnitude that varies with frequency on a linear scale. The frequency scale of the second signal is then translated into a logarithmic scale and deconvolved to determine the size and distribution of moving particles within the scattering medium. The translation and deconvolving requires translation of analog signals to digital signals and subsequent processing by a central processor and a vector signal processor using fast Fourier transfer techniques (FFT). In order to solve for a known particle size distribution of over 80 particle diameters the method just described must sample over 80 frequencies. Even though this method provides an accurate measurement of particle size distribution, it does require a long time period (usually greater than two minutes) to process all of the sample frequencies, due primarily to the stochastic nature of Brownian motion. This technique is best suited for use in a laboratory with samples that have been extracted from a process and properly prepared for measurement analysis. Additionally, this method is strongly dependent upon dispersant viscosity and temperature and the use of non-flowing sample delivery systems. Although this technique provides accurate results for particles having diameters less than 1 micron, it exhibits poor size and volume accuracy for particles above 1 micron.

Another recognized technique and method for measuring the size distribution of very small particles is static light scattering, or angular light scattering. In this method, a collimated monochromatic light beam irradiates an ensemble of particles that flow perpendicularly through the collimated light beam. Light scattered from the particles emerges from the interaction volume over a range of angles from the axis of the collimated beam. The scattered light is collected by a lens placed in the path of the scattered light. The scattered light patterns focused in the focal plane of the lens are typically measured by an array of photodetectors placed in the focal plane. The angular extent of the scatter pattern is determined by the size of the particles. The smaller the particle, the wider the angular extent of the scatter; the larger the particle, the narrower the angular extent of the scatter.

One such method is taught by U.S. Pat. No. 5,416,580 to Trainer, patented on May 16, 1998, which uses multiple light beams to irradiate the particles. This method has demonstrated excellent measurement results for particles in the 0.1 to 3000 micron range in flowing sample systems, without temperature or viscosity dependency. Unlike the dynamic scattering techniques, measurements can be made in less than five seconds with repeatability superior to that of the dynamic light scattering. However, in order to produce good measurement accuracy for a process sample at a high concentration, for example 10% by volume, the process sample must be properly diluted with a dispersant medium to minimize the particle concentration.

The particle concentration capability of static light scattering is limited primarily due to multiple scattering, where primary scattering from a particle does not reach the detector without being re-scattered by at least one other particle. This re-scattering distorts the angular scattering distribution from the ensemble of particles and changes the calculated size distribution. Therefore, presently known static light scattering methods require a sample to be extracted from the process and properly diluted by a dispersing medium for the introduction to a light scattering measurement instrument. In many processes, sample dilution will cause a change in the size distribution.

BRIEF SUMMARY OF THE INVENTION

It is, therefore, an object of the present invention to provide a multiple pathlength sensor used with a particle size distribution apparatus for the accurate measurement of particle size distribution using static light scattering techniques at high particle concentrations.

It is also an object of the present invention to provide a sensor for the accurate measurement of particle size distribution using static light scattering techniques that can be used for the online particle size measurement for process control.

In accordance to the objects, the present invention provides a multiple pathlength sensor that is used in an apparatus that determines the size distribution of small particles contained in a process stream. The apparatus includes a first light delivery arrangement that produces and projects an anamorphically modified first light energy emission and a second light delivery arrangement that produces and projects an anamorphically modified second light energy emission. The apparatus further includes a light collection arrangement for collecting light energy, a detector array receiving the collected light energy and means for translating the detected light energy into particle size distribution.

The sensor of the present invention is installed substantially within the process stream and includes a transparent surface receiving the first and the second light energy emissions projected by said first and said second light delivery arrangements. The first and the second light energy emissions penetrate the transparent surface and enter the sensor in a first directional path. A first light deflecting surface receives the first and the second light energy emissions and modifies the travel of the first and said second light energy emissions into a second directional path through said sensor.

The sensor further includes a first passage that is exposed to the process stream and sized to receive particles of a first predetermined size range. The first light energy emission in the second directional path is projected through the first passage to irradiate the particle ensemble therein. A second passage is exposed to the process stream and sized to receive particles of a second predetermined size range. The second light energy emission in the second directional path is projected through the second passage to irradiate the particle ensemble therein.

A second light deflecting surface receives the light energy projected through the first and second passages and the light energy scattered by the particle ensemble in each of the first and said second passages. The second deflecting surface directionally modifies the light energy it receives into a third directional path through the sensor to the transparent surface, where the light energy escapes the sensor and is collected by the light collection arrangement. The light collected is modified for projection and focus on the detector array.

Output signals representing the angular distribution of the detected scattered light are generated by the detector array and used to determine a measurement of the distribution of the size of the particles contained in the process stream.

BRIEF DESCRIPTION OF THE SEVERAL VIEWS OF THE DRAWINGS

Other objects, features, and advantages of the present invention will be apparent from the following description of a preferred embodiment thereof, taken in conjunction with the sheets of drawings, in which:

FIG. 3A is a perspective view of the multiple pathlength sensor of the present invention;

FIG. 3B is a top plan view of the multiple pathlength sensor of the present invention;

DETAILED DESCRIPTION OF THE INVENTION

Figure 1:
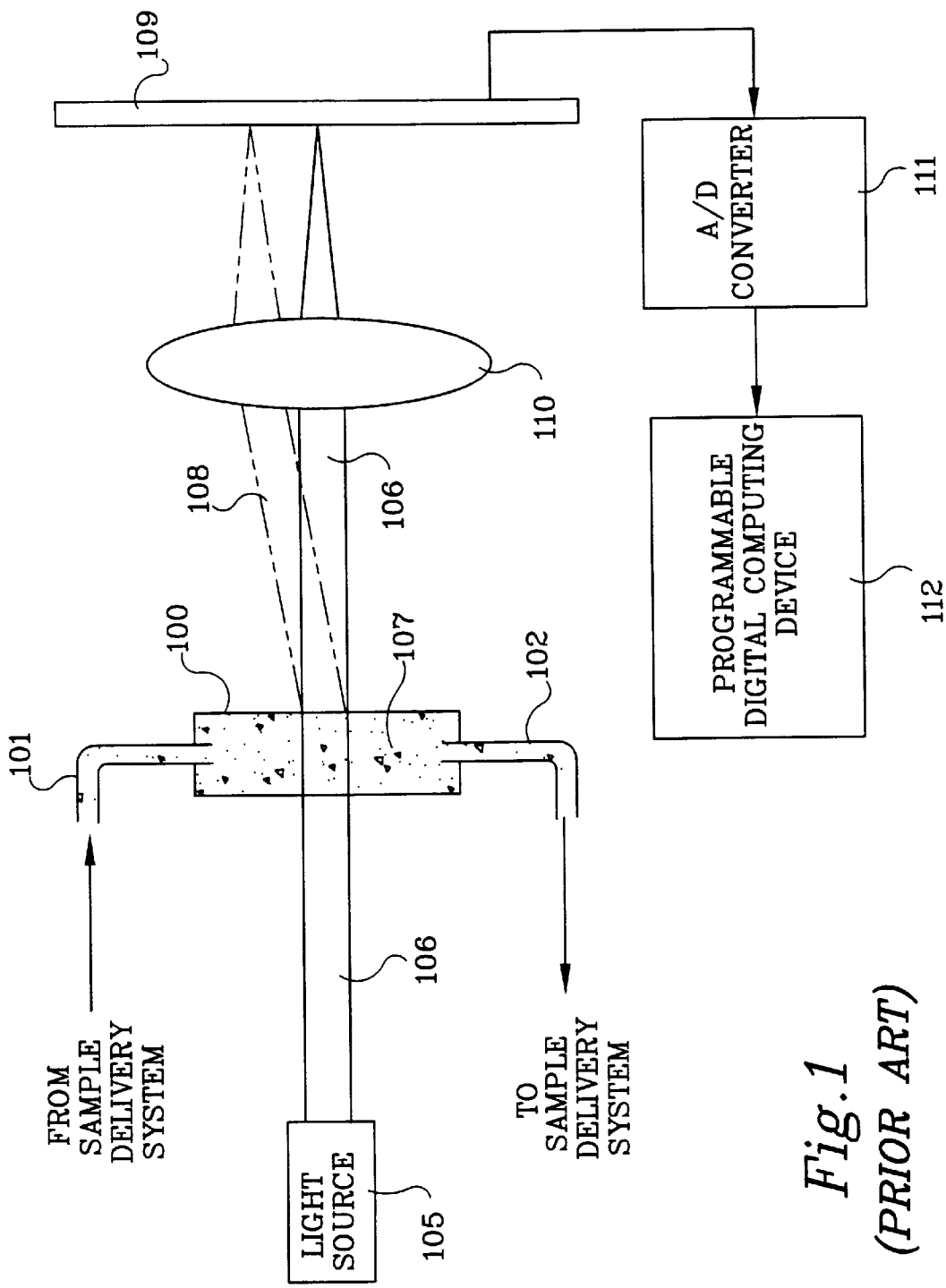
FIG. 1 illustrates, in the form of block diagram, a prior art device for determining the particle size distribution of process stream samples prepared for analysis by diluting the concentration and suspending the particles in a diluting medium.

Although well known by those skilled in the art, a brief description of a presently known apparatus used for obtaining particle size distribution by measuring the angular distribution of scattered light will be set forth in order to help understand the present invention. With reference to FIG. 1, a particle analyzer shown in block diagram operates with a sample delivery system (not shown) that delivers prepared particle samples in a sample stream to a sample cell 100. The particles being measured are typically suspended in a dispersing or diluting medium contained within the sample system. The dispersing medium acts not only as a carrier medium for the particles but also as the required diluting medium to provide the proper dilution of particle concentrations required by the prior art particle analyzer. The sample stream is continually circulated from a reservoir of the sample delivery system into an inlet conduit 101, through sample cell 100 and out of cell 100 via outlet conduit 102 and back to the reservoir. The device of FIG. 1 further includes a light source 105, which generates a light beam (preferably collimated) 106 shown passing through sample cell 100, which contains the particle ensemble 107. Incident light beam 106 and scattered light beam 108 (the product of the light from beam 106 scattered by particles 107) are shown focused on detector array 109 via a single collector lens 110. The detector array 109 outputs analog signals representing the total scattered light intercepted by individual detector elements of the detector array 109. The analog detector array output signals are typically converted to digital signals by A/D conversion techniques by an A/D converter 111 and subsequently processed by a programmable computing device 112 by using well known inversion techniques to obtain the desired particle size distribution.

The static light scattering particle analyzer just described finds disadvantage in that the particle sample must be extracted from the process stream of the manufacturing process and diluted in a dispersant medium for introduction to the particle analyzer. In many processes, particle sample dilution will cause a change in the size distribution. Additionally, the apparatus used to extract the samples jeopardizes the integrity of the manufacturing process stream.

The dilution of the extracted particle samples in a static light scattering particle analyzer is required due primarily to the phenomenon of multiple scattering. That is, in samples of high particle concentration, the light initially scattered from a particle does not reach the detector without being re-scattered by at least one other particle. This re-scattering distorts the angular scattering distribution from the group of particles and changes the calculated size distribution. Multiple scattering is proportional to the product of the particle scattering cross section and the optical pathlength of the sample. Therefore, reducing the sample cell pathlength, while still allowing sufficient space for the largest particles, can reduce the effects of multiple scattering in high concentration particle samples.

The present invention discloses a multiple pathlength sensor having multiple channels or passageways formed thereon that are arranged to be exposed to and contain therein the particle stream. Each channel has a predetermined pathlength that greatly reduces the effects of multiple scattering and, therefore, increases the upper concentration limit that can be effectively used to measure particle size distribution.

Figure 2:
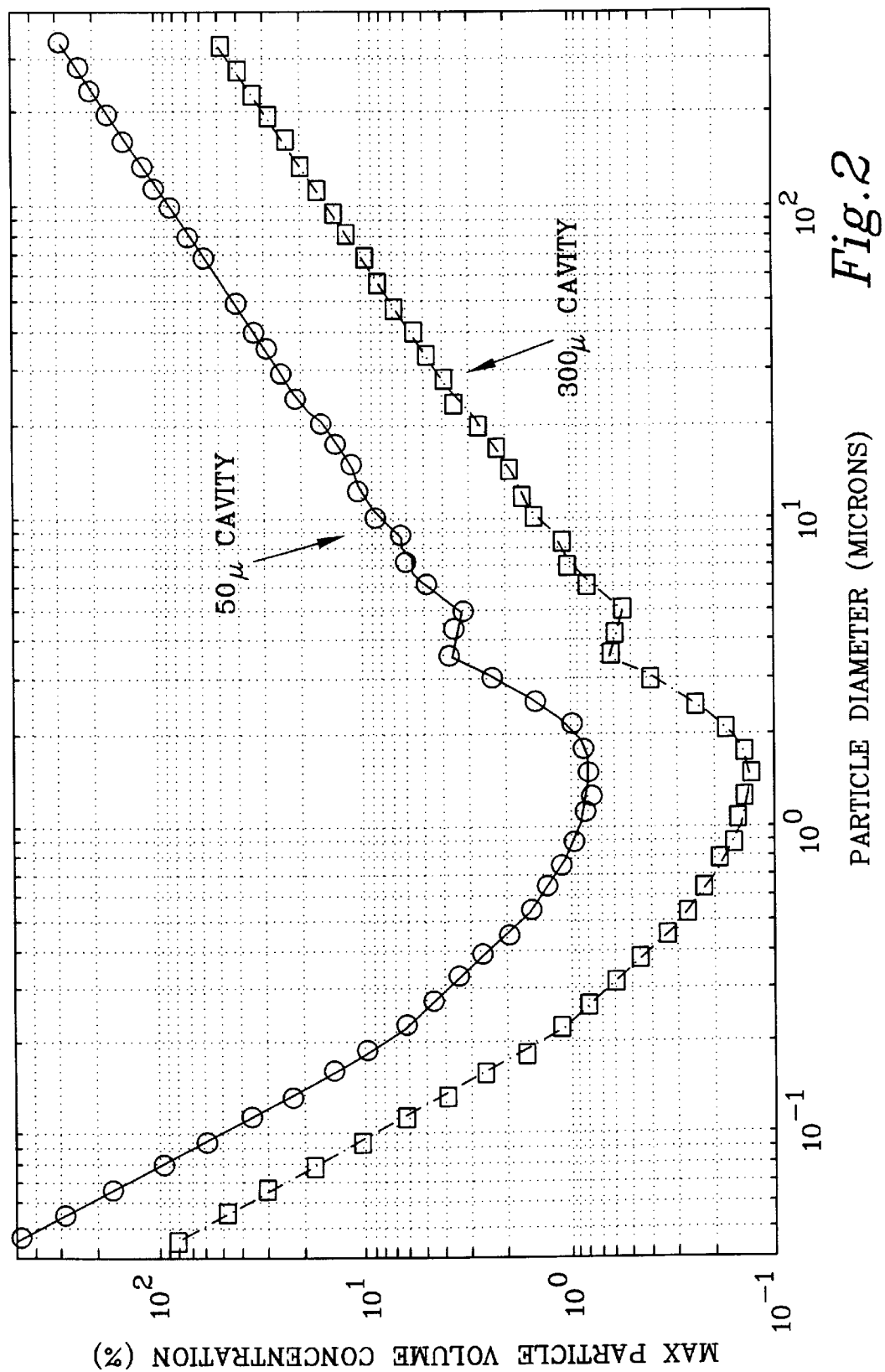
FIG. 2 illustrates, in the form of a graph plot, the theoretical upper concentration limit of two optical channels having pathlengths of 50 and 300 microns.

Turning now to FIG. 2, a graphical representation of the theoretical concentration sampling of two channels having pathlengths of 50 and 300 microns is shown. Using the experimental result of 64% transmission for 0.02% concentration of 1.33 micron particles as a basis, a maximum concentration curve can be generated based upon theoretical scattering cross section per unit volume. The data depicted in FIG. 2 only approximates the true concentration limits, which typically must be calculated from multiple scattering theory; however, it is a reasonable approximation for the explanation of this embodiment.

As can be seen in FIG. 2, the cross section per unit particle volume is inversely proportional to particle diameter for particles above 2 microns in size. In the 50 micron curve a worst case volume concentration limit is shown as 1% at a particle diameter of 1.2 microns, increasing to 10% at 0.2 and 10 microns. The 300 micron channel curve exhibits a scattering cross section per unit volume that decreases for larger particle diameters, allowing for greater than 10% concentration at the 300 micron pathlength for the larger particles.

FIG. 3A and FIG. 3B illustrate the multiple pathlength sensor 10 of the present invention. Sensor 10 includes a first channel 11 and a second channel 12 formed thereon. The first channel 11 of the sensor 10 has a 50 micron width or pathlength and the second channel 12 a 300 micron width or pathlength. It will be appreciated by those skilled in the art that the choice of 50 and 300 micron channels is for purposes of illustration only and the actual optimum channel size will depend on the particle size range and the concentration of the particles contained in the sampled process stream.

Sensor 10 is generally a rectangular structure having sidewalls 13 and 14 extending between a pair of end walls 15 and 16. Sidewalls 13 and 14 extend obliquely from top surfaces 18 and 19, respectively, to a base surface 20. Base surface 20 has a surface area greater than the combined surface areas of top surfaces 18 and 19. As can be seen in FIGS. 3A and 3B, end walls 15 and 16 also extend obliquely from top surfaces 18 and 19 to base surface 20. Channel 11, which is configured in this embodiment to be 50 microns wide, is centrally located between top surfaces 18 and 19, and extends longitudinally from a first opening 22 at end wall 16 to a second opening 21. Opening 21 opens to the said second channel 12, which is 300 microns wide. Channel 12 extends longitudinally from a first opening 23 on end wall 15 to opening 21. The depths of channel 11 and of channel 12 are approximately equal to the pathlength (or the respective width of each channel 11, 12) to provide easy exchange of particles with the sampling stream. Sensor 10 is composed of an optically clear material, such as fused silica or the like. Additionally, sidewalls 13 and 14 are either polished or coated with a suitable reflective material to form reflective surfaces.

Figures 4, 5:
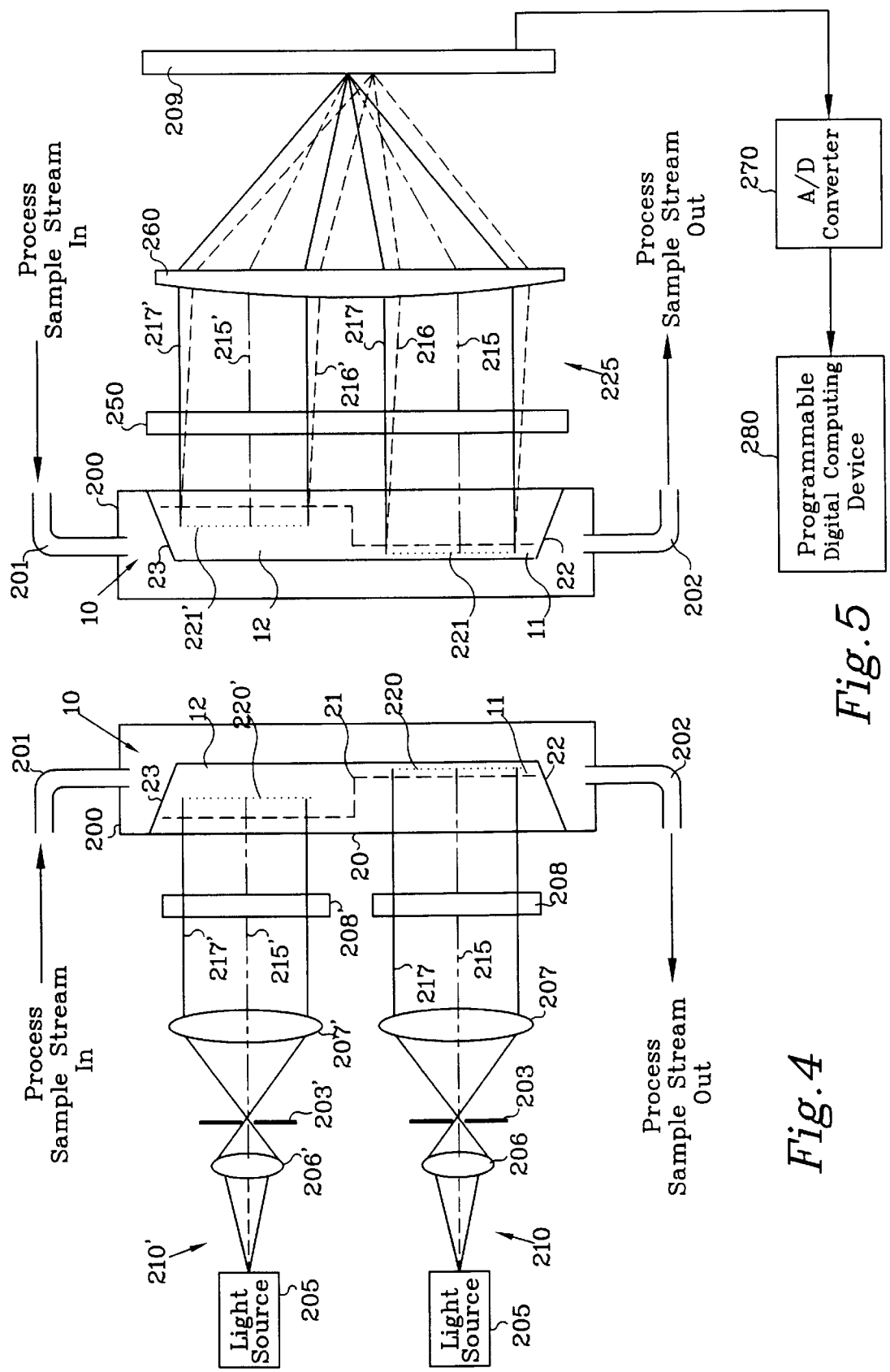
FIG. 4 depicts, in a side block diagram view, the multiple pathlength sensor of FIG. 3A, used in conjunction with the a light delivery arrangement in accordance to the present invention.
FIG. 5 depicts, in a side block diagram view (opposite the side shown in FIG. 4), the multiple pathlength sensor of FIG. 3A, used in conjunction with a light collection arrangement in accordance to the present invention.

Turning now to FIG. 4, the sensor 10 of the present invention is illustrated installed in a sample cell 200. Sample cell 200 receives particle samples in the form of a sample stream from an inlet tube 201. The sample stream flows through sample cell 200 from inlet tube 201 to outlet tube 202. A portion of the sample stream and particle samples contained therein also flow over and through channels 11 and 12 of sensor 10. In the embodiment shown, a portion of the sample stream enters the 300 micron channel 12 at opening 23, flowing through channel 12 to opening 21. The exchange of particles between the sample stream and channels 11 and 12 could be enhanced by ultrasonic air excitation. This stream than enters channel 11 at opening 21 and flows through the 50 micron channel 11 to opening 22, where it exits sensor element 10 and is merged with the main flow in sample cell 200 and exits the sample cell 200 via outlet tube 202. The inlet tube 201 and outlet tube 202 can be connected to a sample delivery system as described in the particle analyzer of FIG. 1, or alternatively, can be connected to a bypass line from the manufacturing process stream. The bypass line would deliver directly to the sample cell 200 a portion of the manufactured process stream and the particles contained therein for analysis.

It will be well understood by those skilled in the art that sensor 10 could also be effectively installed in the aforementioned bypass line or in a conduit conveying the manufacturing process stream and is not limited to an installation within a sampling cell. Any presently known methods for installing the sensor 10 within a sampling cell or conduit may be used. However, within any installation method used, base surface 20 must be either left exposed to receive light or positioned in association with a window allowing light from outside of the conduit to enter the sensor 10 at base surface 20.

The sensor 10 of the present invention is arranged to be used with a light delivery arrangement shown in FIG. 4. The light delivery arrangement includes a first 210 and a second 210' system for delivering light energy to the sensor 10. Each light delivery system 210, 210' is associated with and arranged to deliver light to a respective sensor channel 11, 12. Since each light delivery system is similar, the present invention will be explained using the first light delivery system 210 associated with the 50 micron channel 11. The second light delivery system 210' used to project light energy to the 300 micron channel 12, operates substantially as system 210, except that the beam waist in the channel is larger.

Light energy from a source of light energy 205, such as a laser or laser diode, is received by a first projection lens 206 that focuses the light from source 205 through a spatial filter pinhole 203 onto a collimator lens 207. The collimated light from lens 207 is next applied to a first cylindrical lens 208. Since the light scattered by the sample particles flowing in the sample stream must be measured at small forward scattering angles, the beam divergence in the scattering plane must be minimized. This is accomplished by the use of an anamorphic lens system that produces a focus with a large aspect ratio in one dimension. The light projected from cylindrical lens 208 produces a light beam having a beam waist volume of approximately 50×50×2000 microns. Similarly, the light projected from cylindrical lens 208' produces a light beam having a beam waist volume of approximately 300×300×2000 microns. The anamorphic lens system provides a low divergence in the scattering plane (parallel to the longitudinal dimension of each channel) that increases the sampling volume and provides for a better statistical sampling of the particle samples in channels 11 and 12. A better understanding of this anamorphically modified light energy delivery system may be had by reference to Applicant's co-pending patent application, Ser. No. 09/211, 374 entitled "A SYSTEM FOR DETERMINING SMALL PARTICLE SIZE DISTRIBUTION IN HIGH PARTICLE CONCENTRATIONS", which is incorporated herein by reference.

Figure 6:
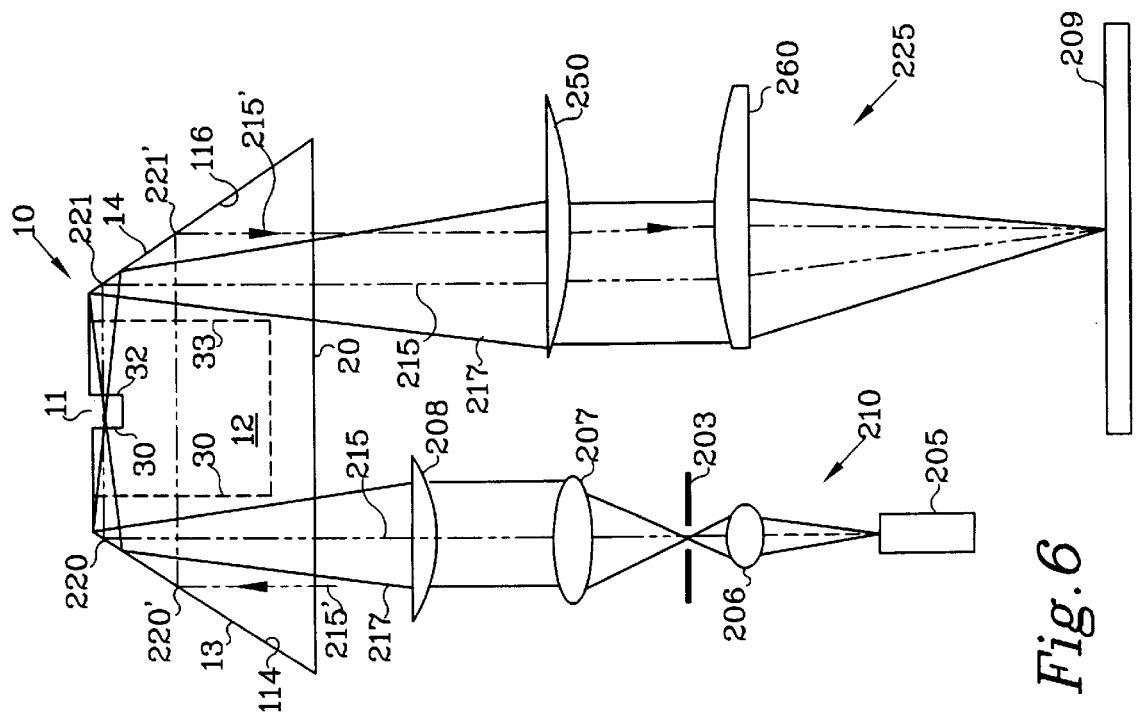
FIG. 6 depicts, in an end block diagram view, the multiple pathlength sensor of the present invention used in conjunction with the light delivery and light collection arrangements in accordance to the present invention.

With reference to FIG. 4 and FIG. 6, the anamorphically modified incident light 217 enters sensor 10 at base surface 20 and is reflected by the inner surface 114 of sidewall 13. The incident light 217 is reflected off of the inner surface 114 and focussed into channel 11 through channel wall 30 and is radiated onto the particles contained in the particle stream flowing in channel 11.

Similarly, the anamorphically modified incident light 217' from the second light delivery system 210' enters sensor 10 at base surface 20 and is reflected from the inner surface 114 of sidewall 13. Again, due to the reflective quality of sidewall 13, the focused light energy is reflected off of the inner surface 114 and projected into channel 12 through channel wall 50. The light exits channel wall 50 and is radiated onto the particles contained in the particle stream flowing in channel 12. This is best illustrated in FIG. 6 by line 215' that represents the optical axis about which incident light 217' travels. For matters of clarity, the elements of the second light delivery system 210', that are shown in FIG. 4 in detail, are not shown in FIG. 6. It will be appreciated by those skilled in the art that the second light delivery system 210' functions similarly to the first light delivery system 210 shown in FIG. 6, except that the larger beam waist fills the larger channel.

With renewed reference to FIG. 6, the incident light 217 and the light scattered by the particles contained in channel 11 enter channel wall 32 and travel to the inner surface 116 of sidewall 14.

As discussed above, due to the width of channel 11 being proximate to the spacing between the particles to be measured, only a minimal amount of re-scattering occurs within channel 11 before the scattered light enters channel wall 32.

With reference now to FIG. 5 as well as FIG. 6, the light collection arrangement 225 used with the present invention will be explained. Incident light 217 and the light scattered by the particles strike the inner surface 116 of side wall 14 along point 221. The light energy striking surface 116 is reflected off of inner surface 116 and exits the sensor from base surface 20 along an optical axis represented by line 215. The light energy exiting base surface 20 is projected onto a second cylindrical lens 250, which recollimates the light energy exiting from sensor 10. Cylindrical lens 250 may be eliminated when the scattered light has high intensity. The collimated incident light 217 and the scattered light 216 from lens 250 are next projected onto a collector lens 260 and focused onto detector array 209 which is in the back focal plane of lens 260. The detector array 209 outputs analog signals representing the total scattered light intercepted by individual detector elements of the detector array 209. The analog detector array output signals are converted to digital signals by A/D converter 270 and are subsequently processed by a programmable computing device 280, using well-known inversion techniques to obtain the desired particle size distribution.

Incident light 217' and scattered light 216' associated with the 300 micron channel 12 enter channel wall 53 and are reflected off of inner surface 116 of sidewall 14 along point 221'. The incident and scattered light exits sensor 10 via base surface 20 as shown in FIG. 6 by the optical axis represented by line 215'. The incident light and scattered light from the 300 micron channel 12 are collected by the light collection arrangement 225 and projected onto detector array 209.

The sensor 10 of the present invention, along with the light delivery 210, 210' and light collection arrangement 225 just described, collectively teach a system well adapted to make a broad range of particle size distribution analyses. The arrangement just described uses a separate light source for each pathlength channel found on the sensor; however, a single light collection arrangement 225 is used. Therefore, it is contemplated that light collection arrangement 225 sequentially collects the incident and scattered light from each channel 11, 12 by activating each light source 205, 205' associated with each light delivery arrangement 210, 210' and recording each corresponding set of scattered light signals in sequence. Consequently, only one detector array 209 and associated A/D converter 270 and processing computer 280 would be required to effectively use the present invention. In such a system, a means for measuring particle sizes between 0.1 and 3000 microns at high concentrations can be effectively made by using a multiple pathlength sensor having the appropriately sized channels. This concept was described with two channels of dissimilar pathlengths, however, it will be appreciated by those skilled in the art that the present invention can be extended to a sensor 10 having any number of appropriately sized channels.

Figure 7:
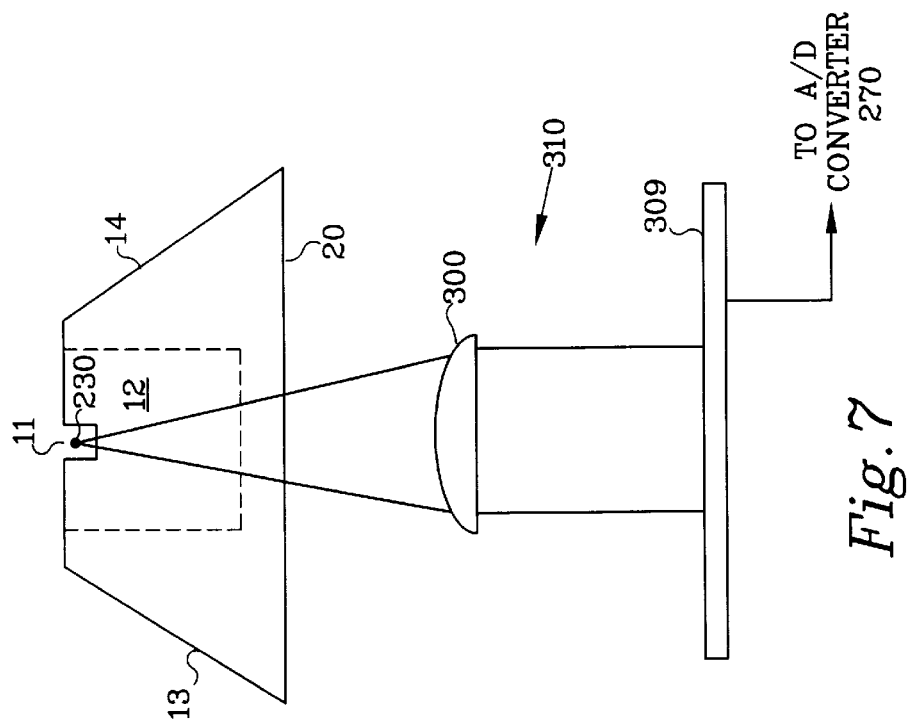
FIG. 7 depicts, in block diagram view, a second light collection arrangement used to collect scattered light at higher scattering angles.

Additionally, as can be seen in FIG. 7, the sensor 10 of the present invention can be used with a second light collection arrangement 310 that includes a collection lens 300 and detector array 309. This second light collection arrangement 310 is used to capture scattered light that exits sensor 10 at higher scattering angles. A single collector lens 300 can be positioned in association with base surface 20 to capture light scattered by particles 230 that are substantially smaller than 0.3 microns. These smaller particles scatter light at higher angles, causing the scattered light to exit the sensor element outside of the optical axis 215 and 215'. Collection lens 300 receives these higher angle scatters and focuses the scattered light collected onto a separate detector array 309 for processing by A/D converter 270 and programmable digital computing device 280.

The present invention has been described with particular reference to the preferred embodiments thereof. It will be obvious that various changes and modifications can be made therein without departing from the spirit and scope of the invention as defined in the appended claims.

What is claimed is:

1. A sensor used in an apparatus for determining the size distribution of small particles contained in a process stream, said apparatus including a first light delivery arrangement for producing and projecting an anamorphically modified first light energy emission and a second light delivery arrangement for producing and projecting an anamorphically modified second light energy emission, a light collection arrangement for collecting light energy, a detector array receiving the collected light energy and means for translating the detected light energy into particle size distribution, said sensor installed substantially within said process stream and comprising:

a) a transparent surface receiving said first and said second light energy emissions projected by said first and said second light delivery arrangements, said first and said second light energy emissions penetrating said transparent surface and entering said sensor in a first directional path;

b) a first light deflecting surface receiving said first and said second light energy emissions entering said sensor in said first directional path and modifying the direction of said first and said second light energy emissions received into a second directional path through said sensor;

c) a first passage exposed to said process stream, said first passage sized to receive particles of a first predetermined size range and said first light energy emission in said second directional path is projected through said first passage to irradiate the particle ensemble therein;

d) at least a second passage exposed to said process stream, said second passage sized to receive particles of a second predetermined size range and said second light energy emission in said second directional path is projected through said second passage to irradiate the particle ensemble therein; and e) a second light deflecting surface receiving said light energy projected through said first and said second passages and the light energy scattered by said particle ensemble in each of said first and said second passages, said second deflecting surface directionally modifying the light energy received into a third directional path through said sensor to said transparent surface, whereby the light energy in said third directional path escapes said sensor and is collected by said light collection arrangement.

2. The sensor as claimed in claim 1, wherein said first and said second light energy emissions in said second directional path are focused within respective first and second passages.

3. The sensor as claimed in claim 2, wherein each of said first and said second passages have a width equal to the optimal pathlength required to reduce multiple scattering of said light energy focused on said particle ensemble in each passage, and each passage having a depth approximately equal to the passage width to allow exchange of particles between said process stream and each passage.

4. The sensor as claimed in claim 1, wherein said sensor is a monolithic structure generally rectangular in cross section and composed of an optically clear material, said sensor further including obliquely oriented first and second sidewalls extending longitudinally between obliquely oriented first and second end walls, said first sidewall prepared to allow the inner surface of said first sidewall to reflect light energy forming said first light deflecting surface and said second sidewall prepared to allow an inner surface of said second sidewall to reflect light energy forming said second light deflecting surface.

5. The sensor as claimed in claim 4, wherein said sensor further includes:

a) first and second top surfaces extending inwardly from a top edge of a respective first and second sidewall toward the center of said sensor defining therebetween the periphery of a first and a second channel, said first and second channels tandemly oriented along a common longitudinal axis with said first channel extending parallel to said first and second sidewalls from a first opening on said first end wall to a second opening on said second channel, and said second channel extending parallel to said first and second sidewalls from a first opening on said second end wall to said second opening of said first channel, whereby said first channel comprises said sensor's first passage and said second channel comprises said sensor's second passage; and b) a planar bottom surface extending perpendicularly between said first and second side walls and said first and second end walls, said bottom surface comprising said transparent surface, whereby said sensor is oriented to allow said anamorphically modified light energy to strike said bottom surface and be transmitted into the interior of said sensor.

6. The sensor as claimed in claim 1, wherein said first light delivery arrangement and said second light delivery arrangement are sequentially activated, whereby said second light energy emission is not projected from said second light projecting arrangement until said light energy in said third directional path escaping said transparent surface and representative of said first light energy emission is collected by said light collection arrangement.

7. The sensor as claimed in claim 1, wherein said apparatus further includes a second light collection arrangement and detector array, said second light collection arrangement disposed to receive and collect the light energy scattered by said particle ensemble of said first and said second passages that are directed to and escape from said transparent surface without being first directionally modified by said second deflecting surface and representative of higher scattering angles.

* * * * *

UNITED STATES PATENT AND TRADEMARK OFFICE
CERTIFICATE OF CORRECTION

PATENT NO.    : 6,104,490
DATED         : August 15, 2000
INVENTOR(S)   : Michael N. Trainer It is certified that error appears in the above-identified patent and that said Letters Patent is hereby corrected as shown below:

Column 5,
Line 64, delete "ultrasonic air excitation" and insert -- ultrasonic excitation --.

Signed and Sealed this

Twenty-seventh Day of November, 2001

Attest:

*Nicholas P. Godici*

NICHOLAS P. GODICI
*Attesting Officer*  *Acting Director of the United States Patent and Trademark Office*